(12) United States Patent
Pocock et al.

(10) Patent No.: US 7,766,188 B2
(45) Date of Patent: Aug. 3, 2010

(54) DOSE INDICATOR DEVICE FOR A FLUID OR POWDERY PRODUCT DISPENSER

(75) Inventors: Andrew Gordon Pocock, Cambridgeshire (GB); Stuart Brian William Kay, Cambridgeshire (GB); Paul Greenhalgh, Cambridgeshire (GB); Wayne O'Hara, Cambridgeshire (GB)

(73) Assignee: Valois S.A.S., Le Neubourg (FR)

( * ) Notice: Subject to any disclaimer, the term of this patent is extended or adjusted under 35 U.S.C. 154(b) by 264 days.

(21) Appl. No.: 11/884,771

(22) PCT Filed: Mar. 14, 2006

(86) PCT No.: PCT/FR2006/050223
§ 371 (c)(1),
(2), (4) Date: Aug. 21, 2007

(87) PCT Pub. No.: WO2006/097659
PCT Pub. Date: Sep. 21, 2006

(65) Prior Publication Data
US 2008/0173669 A1 Jul. 24, 2008

(30) Foreign Application Priority Data
Mar. 16, 2005 (FR) .................... 05 50672

(51) Int. Cl.
*B67D 7/22* (2010.01)
(52) U.S. Cl. .......................................... 222/36; 222/23

(58) Field of Classification Search ................... 222/23, 222/36, 37; 221/2; 116/298; 128/200.23, 128/205.23; 235/116, 375
See application file for complete search history.

(56) References Cited

U.S. PATENT DOCUMENTS

| | | | |
|---|---|---|---|
| 2,465,258 A * | 3/1949 | Nelson | ........................ 235/116 |
| 4,048,949 A | 9/1977 | Schmidt | |
| 4,067,024 A | 1/1978 | Quinn | |
| 4,817,822 A | 4/1989 | Rand et al. | |
| 4,886,010 A | 12/1989 | Stutzman | |

(Continued)

FOREIGN PATENT DOCUMENTS

FR 2 850 192 A 7/2004

(Continued)

*Primary Examiner*—Kevin P Shaver
*Assistant Examiner*—Daniel R Shearer
(74) *Attorney, Agent, or Firm*—Sughrue Mion, PLLC

(57) ABSTRACT

A dose-indicator device for using with a dispenser device for dispensing fluid or powder, in particular a pharmaceutical, so as to indicate the number of doses that have been emitted or that remain to be emitted from the dispenser device, the indicator device comprising a first rotary disk (10) and a second rotary disk (20) that is preferably opaque, said first disk (10) including indicator numbers and/or symbols (11) that are disposed in peripheral manner about the axis of rotation (X) of said first rotary disk (10) around at least two concentric circles, and said second disk (20) including at least one viewing window (21).

21 Claims, 1 Drawing Sheet

U.S. PATENT DOCUMENTS

| | | |
|---|---|---|
| 5,177,712 A | 1/1993 | Kakizawa |
| 5,382,023 A | 1/1995 | Roberts et al. |
| 5,564,414 A | 10/1996 | Walker et al. |
| 5,687,710 A | 11/1997 | Ambrosio et al. |
| 6,082,358 A | 7/2000 | Scarrott et al. |
| 6,240,918 B1 | 6/2001 | Ambrosio et al. |
| 6,283,365 B1 | 9/2001 | Bason |
| 6,328,037 B1 | 12/2001 | Scarrott et al. |
| 6,336,453 B1 | 1/2002 | Scarrott et al. |
| 6,405,727 B1 | 6/2002 | MacMichael et al. |
| 6,543,681 B1 | 4/2003 | Wiederrecht et al. |
| 6,547,763 B2 | 4/2003 | Steenfeldt-Jensen et al. |
| 6,659,307 B1 | 12/2003 | Stradella |
| 6,761,161 B2 | 7/2004 | Scarrott et al. |
| 6,769,601 B2 | 8/2004 | Haikarainen et al. |
| 6,926,002 B2 | 8/2005 | Scarrott et al. |
| 6,953,039 B2 | 10/2005 | Scarrott et al. |
| 7,341,057 B2 | 3/2008 | Scarrott et al. |
| 7,543,582 B2 * | 6/2009 | Lu et al. ................. 128/200.23 |
| 2004/0025870 A1 | 2/2004 | Harrison et al. |
| 2004/0065326 A1 | 4/2004 | MacMichael et al. |
| 2004/0255935 A1 * | 12/2004 | Bruna ................... 128/200.23 |
| 2009/0139516 A1 * | 6/2009 | Augustyn et al. ...... 128/200.23 |

FOREIGN PATENT DOCUMENTS

| | | |
|---|---|---|
| GB | 2 128 390 A | 4/1984 |
| GB | 2 364 649 A | 2/2002 |
| WO | 92/00771 A1 | 1/1992 |
| WO | 97/20589 A1 | 6/1997 |
| WO | 97/30743 A2 | 8/1997 |
| WO | 02/26301 A1 | 4/2002 |

* cited by examiner

DOSE INDICATOR DEVICE FOR A FLUID OR POWDERY PRODUCT DISPENSER

BACKGROUND (1) Field of the Invention

The present invention relates to a dose-indicator device and to a fluid or powder dispenser device including such a dose-indicator device.

(2) Description of Related Art

Dose-indicator devices are well known for indicating to the user the number of doses that have been emitted or that remain to be emitted from a fluid dispenser device, for example, such as a dry-powder inhaler or the like. Indicator devices must satisfy a certain number of requirements. Thus, they must be absolutely reliable, i.e. indicate each dose emitted, so as to avoid any risk of under-counting and/or of over-counting. They must also be suitable for counting any number of doses, in particular a relatively high number of doses, such as sixty doses, for example. In parallel, they must be as compact as possible, so as not to increase excessively the dimensions of the dispenser devices to which they are associated. Naturally, they must be simple and fairly easy to manufacture and to assemble. They must also provide an unambiguous and clearly visible indication of the doses that have been emitted or that remain to be emitted, e.g. through a viewing window provided in the indicator device. Known indicator devices generally present a certain number of drawbacks. A major drawback resides in the fact that while wishing to maintain an overall size that is as small as possible for the indicator device, it must be possible to count a large number of doses, e.g. sixty, which generally results in the indicator numbers or symbols that are to be read by the user being of very small size, with a risk that the user cannot clearly distinguish them, which can in particular be the situation when the user is an elderly person or a person with impaired vision. Depending on the kind of fluid or powder to be dispensed, it is essential for the user to be fully informed about the number of doses that have been emitted or that remain to be emitted, so as to avoid discovering that an appliance is empty during an attack that requires medication to be administered rapidly, for example. A wrong indication, or an indication that is not clearly legible, and that risks being misinterpreted by the user, therefore presents a risk.

BRIEF SUMMARY OF THE PREFERRED EMBODIMENTS OF THE INVENTION

An object of the present invention is to provide a dose-indicator device that does not have the above-mentioned drawbacks.

In particular, an object of the present invention is to provide a dose-indicator device that indicates in clearly visible manner the number of doses that have been emitted or that remain to be emitted.

Another object of the present invention is to provide a dose-indicator device that is as compact as possible, and in particular that has dimensions that are as small as possible, while making it possible to indicate a large number of doses, e.g. about sixty.

Another object of the present invention is to provide an indicator device that is safe and reliable in use, and that is simple and inexpensive to manufacture and to assemble.

The present invention thus provides a dose-indicator device for using with a dispenser device for dispensing fluid or powder, in particular a pharmaceutical, so as to indicate the number of doses that have been emitted or that remain to be emitted from the dispenser device, the indicator device comprising a first rotary disk and a second rotary disk that is preferably opaque, said first disk including indicator numbers and/or symbols that are disposed in peripheral manner about the axis of rotation of said first rotary disk around at least two concentric circles, and said second disk including at least one viewing window.

Advantageously, said second rotary disk includes viewing windows that co-operate successively and/or alternately with indicator numbers and/or symbols that are disposed around different concentric circles.

Advantageously, said second disk includes a plurality of viewing windows that are disposed in peripheral manner about the axis of rotation of said second rotary disk around at least two concentric circles.

Advantageously, the number of concentric circles of indicator numbers and/or symbols on the first rotary disk is identical to the number of concentric circles of viewing windows on the second rotary disk.

Advantageously, said second disk includes at least one set of viewing windows, each set comprising at least two windows that are mutually offset both radially and peripherally.

Advantageously, said second disk includes a plurality of similar sets of viewing windows that are distributed peripherally about the axis of rotation of said disk.

Advantageously, the axes of rotation of the first and second rotary disks are mutually offset.

Advantageously, the diameter of the first disk is greater than the diameter of the second disk.

Advantageously, said first and second rotary disks are tangential at a point on their outer peripheries.

Advantageously, said second disk is superposed on said first disk, said two disks co-operating with a stationary viewing slot of the device, such that a respective indicator number and/or symbol of the first disk is visible in said viewing slot, through a respective viewing window of the second disk.

Advantageously, the positions of the indicator numbers and/or symbols on the first disk and the positions of the viewing windows on the second disk are predetermined, such that each time the device is actuated, a single indicator number and/or symbol is visible in said stationary viewing slot of the device, through a single viewing window of the second disk.

Advantageously, said first disk includes a first peripheral set of teeth that co-operates with actuator means that are adapted to cause said first disk to turn about its axis of rotation and a second peripheral set of teeth, said second disk including a third peripheral set of teeth that co-operates with said second peripheral set of teeth of said first disk, such that turning the first disk causes the second disk to turn.

Advantageously, on said first disk, each indicator number and/or symbol occupies a space having a surface area of at least 8 square millimeters (mm$^2$), advantageously at least 10 mm$^2$, and preferably at least 12 mm$^2$.

Advantageously, said first disk includes at least sixty indicator numbers and/or symbols, advantageously sixty-three, distributed around three concentric circles about the axis of rotation of the first disk.

Advantageously, said second disk includes twenty-one viewing windows forming seven sets of three windows, said seven sets being distributed peripherally about the axis of rotation of the second disk, said three windows of each set being mutually offset both radially and peripherally.

Advantageously, said first disk has a diameter of about 55 millimeters (mm) and/or the second disk (20) has a diameter of about 45 mm.

Advantageously, each time the device is actuated, the first disk (10) is caused to turn through an angle α, and the second disk (20) is caused to turn simultaneously through an angle 3α/2.

Advantageously, the angle α is equal to 22.86° and the angle 3α/2 is equal to 34.28°.

The present invention also provides a fluid or powder dispenser device including a dose-indicator device as described above.

Advantageously, the indicator device is actuated each time the fluid dispenser device is actuated.

BRIEF DESCRIPTION OF THE DRAWINGS

These characteristics and advantages and others of the present invention appear more clearly from the following detailed description of an advantageous embodiment thereof, given by way of non-limiting example, and with reference to the accompanying drawing, in which.

DETAILED DESCRIPTION OF THE PREFERRED EMBODIMENTS

The present invention relates to a dose-indicator device for using with a fluid or powder dispenser device, such as a dry-powder inhaler, and that makes it possible to indicate to the user the number of doses that have been emitted or that remain to be emitted. Naturally, the indicator device of the present invention applies to any type of fluid or powder dispenser device, such that the dispenser device is not described in detail below. Only the portions of the dispenser device that receive the indicator device, and the means for actuating said dispenser device are described succinctly below. With this information, the person skilled in the art is capable of applying the indicator device of the present invention to any chosen type of fluid or powder dispenser device.

Figures 1, 2:
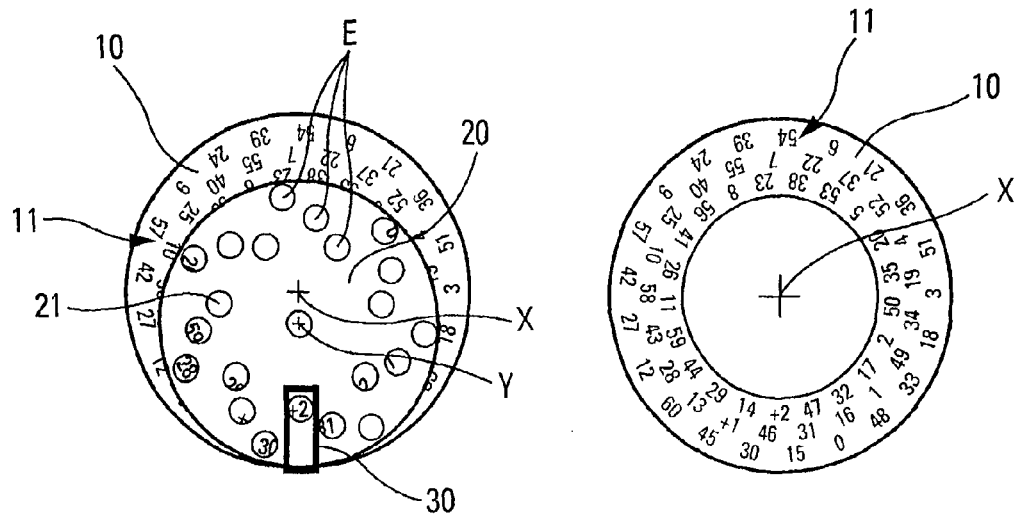
FIG. 1 is a diagrammatic plan view of a dose-indicator device constituting an advantageous embodiment of the present invention.
FIG. 2 is a view similar to the FIG. 1 view showing the first rotary disk only.

With reference to the figures, the dose-indicator device of the invention comprises a first rotary disk 10 and a second rotary disk 20. The second rotary disk 20 is preferably opaque, and it is preferably superposed on said first rotary disk 10. The axis of rotation X of the first rotary disk 10 is advantageously offset relative to the axis of rotation Y of the second rotary disk 20, as can be seen in FIG. 1. In addition, the second rotary disk 20 preferably has a diameter that is less than the diameter of the first rotary disk 10. The first and second rotary disks 10, 20 touch at a point on their outer peripheries, as can be seen clearly in FIGS. 1 and 5.

Figure 3:
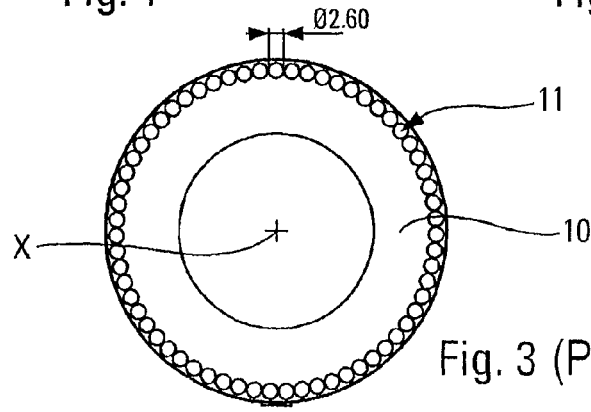
FIG. 3 is a view similar to the FIG. 2 view showing a known rotary disk of the prior art.

The first rotary disk 10 includes indicator numbers and/or symbols 11 that are disposed in peripheral manner about the axis of rotation X around at least two concentric circles, preferably around three concentric circles as shown in FIG. 2. The second rotary disk 20 includes at least one, and preferably a plurality of viewing windows 21 that advantageously co-operate successively and/or alternately with indicator numbers and/or symbols 11 that are disposed around different concentric circles of the first rotary disk 10. This embodiment, that provides indicator numbers and/or symbols that are radially offset, makes it possible to produce indicator numbers and/or symbols that are larger, and therefore easier to read for the user. In particular, the embodiment shown in the figures and described in greater detail below makes it possible to provide indicator numbers and/or symbols that are capable of occupying a space on the first rotary disk 10 of at least 8 mm$^2$, advantageously at least 10 mm$^2$, and preferably at least 12 mm$^2$. The embodiment shown in the figures, and in particular in FIG. 2, makes it possible, in reality, to dispose the indicator numbers and/or symbols in circles that are 4 mm in diameter, thereby making a surface area of 12.56 mm$^2$, or even in a square having sides that are 4 mm, i.e. a surface area of 16 mm$^2$. In comparison, FIG. 3 shows a rotary disk 10 of the same size, turning about an axis of rotation X and including the same number of indicator numbers and/or symbols 11 distributed around its periphery around a single circle. In this event, each indicator number and/or symbol 11 occupies a circular surface area that is 2.6 mm in diameter, i.e. a surface area of 5.30 mm$^2$. At best, if squares of side 2.6 mm are considered, the maximum surface area occupied by the indicator numbers and/or symbols 11 of the disk in FIG. 3 does not exceed 6.76 mm$^2$. Therefore, it should be observed that the present invention makes it possible to provide indicator numbers and/or symbols that are much larger, and therefore much more visible to the user. The risk of the user misreading the indicator is therefore greatly reduced, or even completely eliminated.

Preferably, the second indicator disk 20 includes a plurality of viewing windows 21 that are also disposed in peripheral manner about the axis of rotation Y of the second rotary disk 20 around at least two concentric circles, preferably around three concentric circles as shown in FIG. 1. The number of concentric circles provided for the indicator numbers and/or symbols 11 on the first rotary disk 10 is advantageously equal to the number of concentric circles provided for the viewing windows 21 on the second rotary disk 20. Naturally, the embodiment shown is only an example, and a different number of concentric circles, e.g. two, four, or more, can be envisaged. The viewing windows 21 of the second rotary disk 20 are advantageously disposed in at least one set E, each set E comprising at least two windows 21 that are mutually offset both radially and peripherally. A plurality of similar sets E of viewing windows are advantageously provided, said sets being distributed peripherally about the axis of rotation Y of the second rotary disk 20. In the embodiment shown in FIGS. 1 and 5, there are seven sets E, each comprising three viewing windows 21 that are mutually offset both radially and peripherally.

The second rotary disk 20 is therefore superposed, preferably on the first rotary disk 10, and the two rotary disks co-operate with a stationary viewing slot 30 of the device, so as to display an indicator number and/or symbol in said viewing slot 30, through a viewing window 21 of the second rotary disk 20. The other indicator numbers and/or symbols 11 are not visible to the user, being masked either by the second opaque disk 20, or by the portion of the dispenser device surrounding the stationary viewing slot 30. In the embodiment shown in FIG. 1, it is the symbol + and the number 2 that are displayed in the viewing slot 30. With reference to FIG. 2, it should be observed that the embodiment shown shows an indicator device in which counting-down takes place from 60 to 0, the two strokes (or actuations) before the first real use representing priming and being marked by the indications +2 and +1, for showing the user that the first two actuations, that are likely to form incomplete doses, or else that correspond to test strokes, must not be inhaled. In this event and by way of example, the indications +1 and +2 can be shown in a different color code, possibly green. Similarly, towards the end, i.e. the last five doses to be emitted, the numbers 5, 4, 3, 2, 1, and 0 can also be shown in a different color code, e.g. red, so as to warn the user that the device is nearly empty. It should be observed that the distribution of the indicator numbers and/or symbols on the first rotary disk 10 advantageously corresponds substantially to the distribution of the viewing windows 21 on the second rotary disk 20, in that successive numbers are offset both radially, i.e. disposed around different concentric circles, and peripherally around the first rotary disk 10.

In operation, one of the two rotary disks turns while the fluid dispenser device is being actuated. The rotary disk in question is preferably the first rotary disk 10. Coupling means are advantageously provided between the first rotary disk 10 and the second rotary disk 20 so as cause the second rotary disk 20 to turn simultaneously. On each actuation, the first rotary disk 10 therefore turns relative to the stationary viewing slot 30 so as to display the following number in the viewing slot 30, and, simultaneously, the second rotary disk 20 also turns so as to come to co-operate with the appropriate number of the first rotary disk, while masking the remainder of the viewing slot 30. In practice, in the embodiment shown having three concentric circles referenced 11 and viewing windows 21, the display in the viewing slot 30 for three successive doses is situated in three different positions in said viewing slot 30, i.e. a top position, as shown in FIG. 1, a central position, and a bottom position. The dose that follows the dose displayed in the bottom position in the stationary viewing slot 30 is once again displayed in the top position. In reality, this corresponds to the sets E of viewing windows 21 that successively display successive dose numbers in different radial positions in the stationary viewing slot 30. When passing on to the following set E, the same sequence begins and so on.

In the specific embodiment shown in FIGS. 1 and 2 including sixty-three indicator numbers and/or symbols and twenty-one viewing windows, and with first and second rotary disks that advantageously have respective diameters of about 55 mm and 45 mm, each time the device is actuated, the first rotary disk 10 is caused to turn through an angle α, and the second disk 20 is caused to turn simultaneously through an angle 3α/2. More precisely, in this embodiment, the angle α is equal to 22.86° and the angle 3α/2 is equal to 34.28°. Naturally, with a different number of doses and/or with different disk dimensions, the distribution of the indicator numbers and/or symbols could be different, and all of the parameters could thus be adapted so as to obtain, once again, an optimum size for each indicator number and/or symbol written on the first rotary disk 10. The same applies for the distribution of the viewing windows 21 on the second rotary disk 20. A mathematical model makes it possible to optimize the relationships between the dimensions of the rotary disks 10, 20, the number of doses to be indicated, and the resulting positions and sizes of the indicator numbers and/or symbols 11 on the first rotary disk 10, and of the viewing windows on the second rotary disk 20. Changing the shape(s) and size(s) of one or more sets of teeth 15, 16, 26 also provides an adjustable parameter.

The present invention therefore makes it possible to provide larger indicator numbers and/or symbols on a single disk, thereby simplifying the manufacture, assembly, and operation of the indicator device, while providing the user with information that is more legible.

Figures 4, 5:
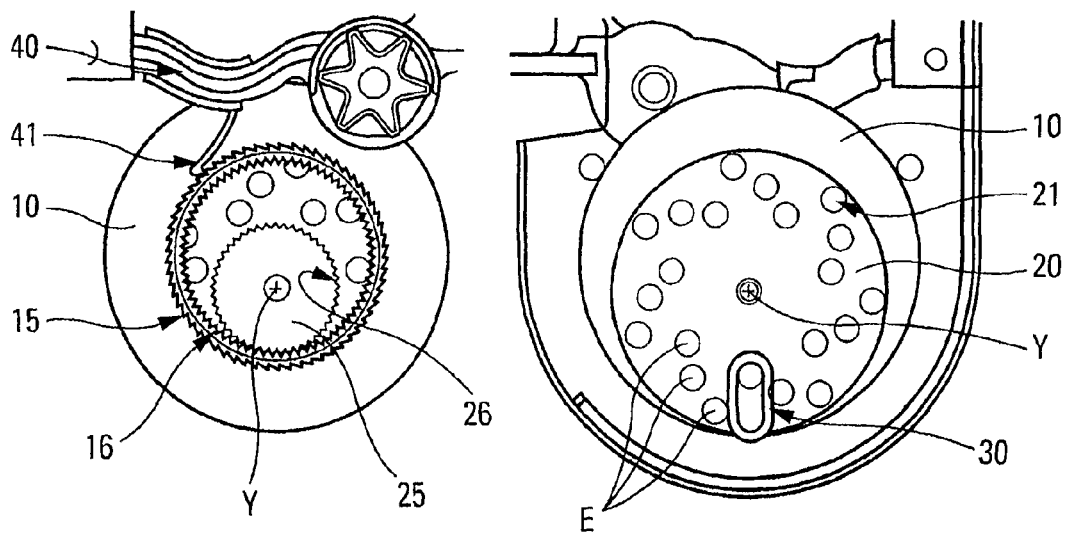
FIG. 4 is a diagrammatic view from below showing the actuator means of the indicator device.
FIG. 5 is a view similar to the FIG. 1 view showing an indicator device installed in a fluid or powder dispenser device.

FIG. 4 shows an embodiment of actuator means of the indicator device of the present invention. In this embodiment, a flexible tab 41 secured to an actuator portion 40 of the fluid dispenser device co-operates with a first peripheral set of teeth 15, in this embodiment an outer set of teeth, provided on the first rotary disk 10. The first rotary disk 10 further includes a second peripheral set of teeth 16, in this embodiment an inner set of teeth, that co-operates with a third peripheral set of teeth 26 provided on the second rotary disk 20. In FIG. 4, which is a diagrammatic view from below, it should be observed that the first rotary disk 10 advantageously is not solid, but, rather, has a hole in its center, such that the portion of the second rotary disk 20 that includes the set of teeth 26 on its periphery penetrates into the central opening of the first rotary disk 10, said central opening having an edge that is formed by the second set of teeth 16. In this way, each time the resilient tab 41 causes the first rotary disk 10 to turn, said first rotary disk causes the second rotary disk 20 to turn by means of the second set of teeth 16 co-operating with the third set of teeth 26. Naturally, other actuator means can thus be envisaged. Naturally, anti-return means and the like can be provided so as to prevent the disks from turning in the opposite direction to the direction imposed by the actuator means.

Although the present invention is described above with reference to a particular embodiment thereof, it is clear that it is not limited by said embodiment, and on the contrary, any useful modification could be applied thereto by a person skilled in the art, without going beyond the ambit of the present invention, as defined by the accompanying claims.

The invention claimed is:

1. A dose-indicator device for using with a dispenser device for dispensing fluid or powder, in particular a pharmaceutical, so as to indicate the number of doses that have been emitted or that remain to be emitted from the dispenser device, the indicator device being characterized in that it comprises a first rotary disk (10) and a second rotary disk (20), said first disk (10) including indicator numbers and/or symbols (11) that are disposed in peripheral manner about an axis of rotation (X) of said first rotary disk (10) around at least two concentric circles, and said second disk (20) including a plurality of viewing windows (21);

wherein the plurality of viewing windows (21) are disposed in a peripheral manner about an axis of rotation (Y) of said second rotary disk (20) around at least two concentric circles;

wherein the number of concentric circles of indicator numbers and/or symbols (11) on the first rotary disk (10) is identical to the number of concentric circles of viewing windows (21) on the second rotary disk (20).

2. The device according to claim 1, wherein the viewing windows (21) cooperate successively and/or alternately with indicator numbers and/or symbols (11) that are disposed around different concentric circles.

3. The device according to claim 1, wherein the viewing windows comprise a plurality of sets (E) of viewing windows (21), each set (E) comprising at least two of the viewing windows (21) that are mutually offset both radially and peripherally.

4. The device according to claim 3, in which said second disk (20) includes a plurality of similar sets (E) of viewing windows (21) that are distributed peripherally about the axis of rotation (Y) of said disk (20).

5. The device according to claim 1, in which the axes of rotation (X, Y) of the first and second rotary disks (10, 20) are mutually offset.

6. The device according to claim 1, in which the diameter of the first disk (10) is greater than the diameter of the second disk (20).

7. The device according to claim 6, in which said first and second rotary disks (10, 20) are tangential at a point on their outer peripheries.

8. The device according to claim 1, in which said second disk (20) is superposed on said first disk (10), said two disks (10, 20) co-operating with a stationary viewing slot (30) of the device, such that a respective indicator number and/or symbol (11) of the first disk (10) is visible in said viewing slot (30), through a respective viewing window (21) of the second disk (20).

9. The device according to claim 8, in which the positions of the indicator numbers and/or symbols (11) on the first disk (10) and the positions of the viewing windows (21) on the second disk (20) are predetermined, such that each time the device is actuated, a single indicator number and/or symbol (11) is visible in said stationary viewing slot (30) of the device, through a single viewing window (21) of the second disk (20).

10. The device according to claim 1, in which said first disk (10) includes a first peripheral set of teeth (15) that co-operates with actuator means (40, 41) that are adapted to cause said first disk (10) to turn about its axis of rotation (X) and a second peripheral set of teeth (16), said second disk (20) including a third peripheral set of teeth (26) that co-operates with said second peripheral set of teeth (16) of said first disk (10), such that turning the first disk (10) causes the second disk (20) to turn.

11. The device according to claim 1, in which, on said first disk (10), each indicator number and/or symbol (11) occupies a space having a surface area of at least 8 mm².

12. The device according to claim 1, in which said first disk (10) includes at least sixty indicator numbers and/or symbols (11), advantageously sixty-three, distributed around three concentric circles about the axis of rotation (X) of the first disk (10).

13. The device according to claim 1, in which said second disk (20) includes twenty-one viewing windows (21) forming seven sets (E) of three windows (21), said seven sets (E) being distributed peripherally about the axis of rotation (Y) of the second disk (20), said three windows (21) of each set (E) being mutually offset both radially and peripherally.

14. The device according to claim 1, in which said first disk (10) has a diameter of about 55 mm and/or the second disk (20) has a diameter of about 45 mm.

15. The device according to claim 1, in which, each time the device is actuated, the first disk (10) is caused to turn through an angle $\alpha$, and the second disk (20) is caused to turn simultaneously through an angle $3\alpha/2$.

16. The device according to claim 15, in which the angle $\alpha$ is equal to 22.86° and the angle $3\alpha/2$ is equal to 34.28°.

17. The fluid or powder dispenser device, characterized in that it includes a dose-indicator device according to claim 1.

18. The fluid or powder dispenser device according to claim 17, in which the indicator device is actuated each time the fluid dispenser device is actuated.

19. The device according to claim 1, wherein the second rotary disk is opaque.

20. The device according to claim 1, wherein, on said first disk, each indicator number and/or symbol occupies a space having a surface area of at least at least 10 mm².

21. The device according to claim 1, wherein, on said first disk (10), each indicator number and/or symbol occupies a space having a surface area of at least 12 mm².

* * * * *